United States Patent
Nguyen et al.

(10) Patent No.: US 12,361,556 B1
(45) Date of Patent: Jul. 15, 2025

(54) COMPUTE SYSTEM WITH HEAD AILMENT DIAGNOSTIC MECHANISM AND METHOD OF OPERATION THEREOF

(71) Applicant: BelleTorus Corporation, Cambridge, MA (US)

(72) Inventors: Thi Thu Hang Nguyen, Toulouse (FR); Léa Mathilde Gazeau, Toulouse (FR); Jonathan Wolfe, Plymouth Meeting, PA (US)

(73) Assignee: BelleTorus Corporation, Cambridge, MA (US)

( * ) Notice: Subject to any disclaimer, the term of this patent is extended or adjusted under 35 U.S.C. 154(b) by 0 days.

(21) Appl. No.: 18/962,234

(22) Filed: Nov. 27, 2024

(51) Int. Cl.
*G06T 7/00* (2017.01)
*A61B 5/00* (2006.01)
*G06T 7/11* (2017.01)
*G16H 50/30* (2018.01)

(52) U.S. Cl.
CPC ............ *G06T 7/0012* (2013.01); *A61B 5/448* (2013.01); *A61B 5/7264* (2013.01); *G06T 7/11* (2017.01); *G16H 50/30* (2018.01); *G06T 2207/20081* (2013.01); *G06T 2207/30088* (2013.01)

(58) Field of Classification Search
CPC ....... A61B 5/448; A61B 5/0077; A61B 5/446; A61B 5/0064; A61B 5/7264; A61B 8/0858; G06T 7/0012; G06T 2207/30088; G06T 2207/30004; G06T 2207/10004; G06T 2207/20021; G06T 2207/20081; G06T 2207/10056; G06T 7/11; G06T 7/33; G06N 3/08; G06N 20/00; G16H 50/20; G16H 50/30; G06F 18/24; G06F 18/214;
(Continued)

(56) References Cited

U.S. PATENT DOCUMENTS 11,257,579 B2   2/2022  Purushothaman et al.
11,282,190 B2*  3/2022  Niebauer .............. G06N 20/00
11,508,168 B2  11/2022  Allen et al.
(Continued)

FOREIGN PATENT DOCUMENTS

KR    20220096238 A1 *  7/2022  ............. A61B 5/448
KR    20230166568 A   * 12/2023
WO    WO-2019134760 A1 *  7/2019  ............. A61B 5/448

OTHER PUBLICATIONS

Aggio, D., Dixon, C., Law, E.H. et al. Estimation of health utility values for alopecia areata. Qual Life Res 33, 1581-1592 (2024). https://doi.org/10.1007/s11136-024-03645-9 (Year: 2024).*
(Continued)

*Primary Examiner* — Aaron W Carter
*Assistant Examiner* — Courtney Joan Nelson
(74) *Attorney, Agent, or Firm* — Perspectives Law Group, Corp.

(57) ABSTRACT

A method of operation of a compute system includes: receiving patient images by an head ailment artificial intelligence (AI) including a multi-task decoder block; concurrently generating a scalp segmentation and a hair loss heat map from the multi-task decoder block of the head ailment AI; generating a composite hair loss image based on the hair loss heat map and a quadrant computation of the scalp segmentation; and generating a SALT score based the hair loss heat map and the composite hair loss image for displaying on a device.

20 Claims, 9 Drawing Sheets
(6 of 9 Drawing Sheet(s) Filed in Color)

(58) Field of Classification Search
CPC .... G06F 18/241; G06V 40/10; G06V 40/168; G06V 2201/03; G06V 40/172
See application file for complete search history.

(56) References Cited

U.S. PATENT DOCUMENTS

| | | |
|---|---|---|
| 11,806,555 B2 | 11/2023 | Christiano et al. |
| 2017/0032223 A1* | 2/2017 | Zingaretti ............ A61B 5/7275 |
| 2020/0160032 A1 | 5/2020 | Allen et al. |
| 2021/0343384 A1 | 11/2021 | Purushothaman et al. |
| 2022/0223293 A1 | 7/2022 | Steinberg-Koch et al. |
| 2023/0043374 A1 | 2/2023 | Christiano et al. |
| 2024/0032856 A1* | 2/2024 | Park ....................... G16H 50/20 |

OTHER PUBLICATIONS

Machine translation obtained from google patents of KR20230166568A (Year: 2023).*

Machine translation obtained from google patents of KR20220096238A1 (Year: 2022).*

* cited by examiner

COMPUTE SYSTEM WITH HEAD AILMENT DIAGNOSTIC MECHANISM AND METHOD OF OPERATION THEREOF

TECHNICAL FIELD

An embodiment of the present invention relates generally to a compute system, and more particularly to a system with a head ailment diagnostic mechanism.

BACKGROUND

A head ailment can manifest in many different ways. By way of an example, Alopecia areata (AA) is a complex autoimmune condition that causes nonscarring hair loss. Current data suggest 34%-50% of patients recover within 1 year, while 14%-25% of patients will progress to AT (alopecia totalis) or AU (alopecia universalis), at which point patients rarely fully recover. The exact pathophysiology of the disease is currently unknown. However, evidence suggests that AA is caused by an autoimmune reaction to the hair follicles due to both genetic and environmental factors.

Thus, a need still remains for a compute system with a head ailment diagnostic mechanism to provide guidelines for clinical research in head ailment has allowed for quantification of disease to standardize the quantification of hair loss across the different quadrants of the head. In view of the ever-increasing commercial competitive pressures, along with growing healthcare needs, healthcare expectations, and the diminishing opportunities for meaningful product differentiation in the marketplace, it is increasingly critical that answers be found to these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

An embodiment of the present invention provides a method of operation of a compute system including: receiving patient images by a head ailment artificial intelligence (AI) including a multi-task decoder block; concurrently generating a scalp segmentation and a hair loss heat map from the multi-task decoder block of the head ailment AI analyzing the patient images; generating a composite hair loss image based on the hair loss heat map and a quadrant computation of the scalp segmentation; and generating a SALT score based the hair loss heat map and the composite hair loss image for displaying on a device.

An embodiment of the present invention provides a compute system, including a control circuit, including a processor, configured to: receive patient images by an head ailment artificial intelligence (AI) including a multi-task decoder block; concurrently generate a scalp segmentation and a hair loss heat map from the multi-task decoder block of the head ailment AI analysis of the patient images; generate a composite hair loss image based on the hair loss heat map and a quadrant computation of the scalp segmentation; and generate a SALT score based the hair loss heat map and the composite hair loss image for displaying on a device.

An embodiment of the present invention provides a non-transitory computer readable medium including instructions for a compute system, including: receiving patient images by an head ailment artificial intelligence (AI) including a multi-task decoder block; concurrently generating a scalp segmentation and a hair loss heat map from the multi-task decoder block of the head ailment AI analyzing the patient images; generating a composite hair loss image based on the hair loss heat map and a quadrant computation of the scalp segmentation; and generating a SALT score based the hair loss heat map and the composite hair loss image for displaying on a device.

Certain embodiments of the invention have other steps or elements in addition to or in place of those mentioned above. The steps or elements will become apparent to those skilled in the art from a reading of the following detailed description when taken with reference to the accompanying drawings.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
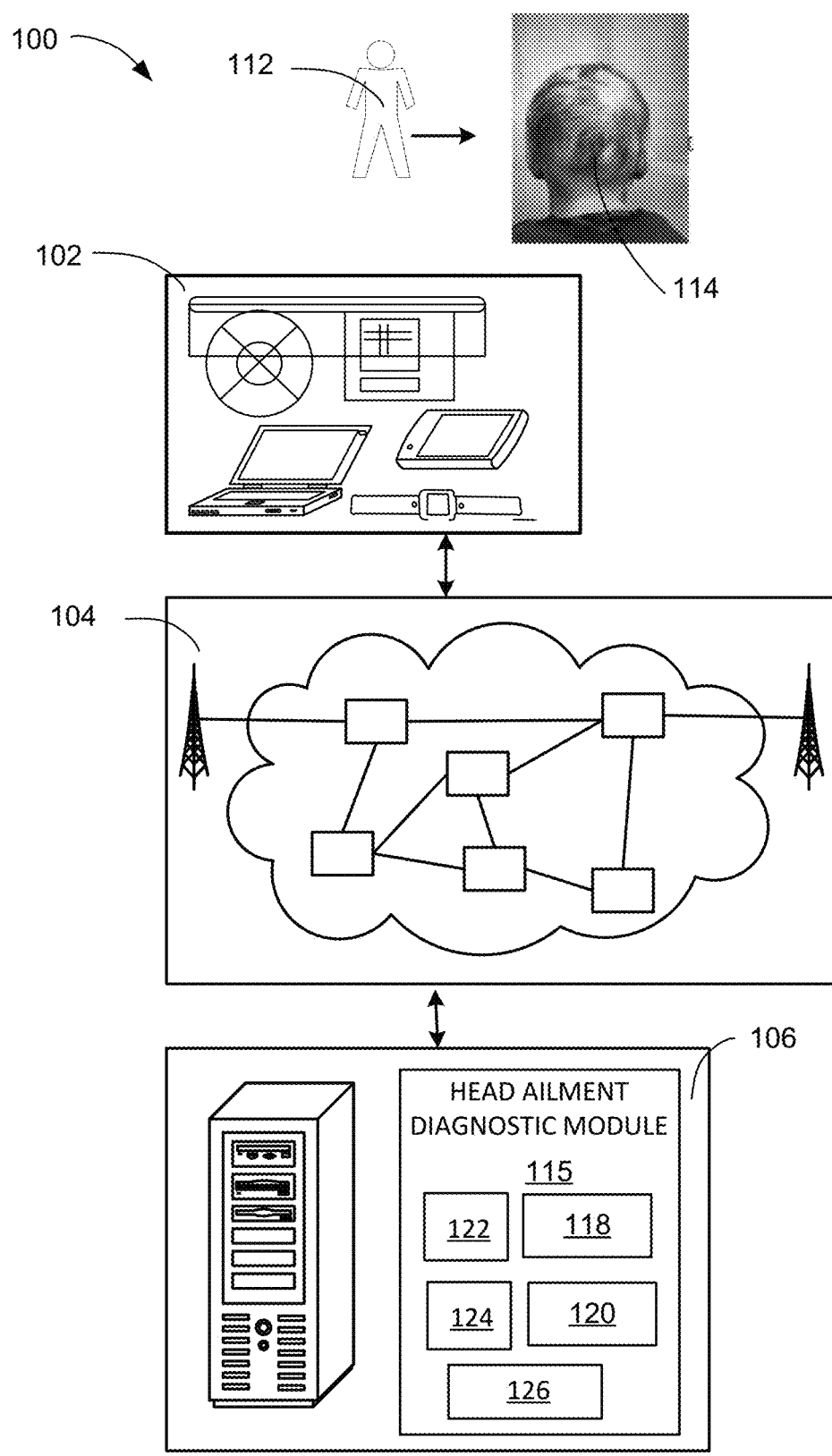
FIG. 1 is an example of a system architectural diagram of a compute system with a head ailment diagnostic mechanism in an embodiment of the present invention.

A head ailment AI system has two main parts. The first part is a deep learning model whose input is a head image. There are two outputs: scalp segmentation and a heat-map (result of a regression task) which shows the percentage of hair loss on that given image. A multi-task learning is used for this model because of the high correlation between two tasks. This approach also reduces the inference time since only one model is run at a time instead of two. In the second part of the system, is to compute the percentage of hair loss based on the heat-map output of the first part. If the view is given, the system will find the corresponding quadrant of the view and compute a SALT score. The head ailment AI system is tested with 188 images containing 47 sets of patients 112 with Alopecia, four views (left, right, top, back)

for each set. The head ailment AI system got an ICC of 0.95 for the agreement between doctors and head ailment AI system.

Randomized controlled trials have recently been completed for the management of Alopecia Areata (AA). The addition of the Severity of Alopecia Tool (SALT) which provides guidelines for clinical research in AA has allowed for quantification of disease. Recent therapeutic breakthroughs with Janus kinase (JAK) inhibitors have led to increased investigation for potential treatment options for this condition. The Severity of Alopecia Tool was developed to standardize the quantification of hair loss across the different quadrants of the head. The lack of standardization of hair loss is a glaring inconsistency amongst studies leading to investigatory and observational biases.

Multi-task learning requires training a model to solve more than one task simultaneously. In other words, when optimized more than one loss function, the model is multi-tasking. This type of learning can improve the accuracy and consistency of the model. There are two main types of multi-task learning including hard parameter sharing and soft parameter sharing. The hard parameter sharing is the model sharing almost all layers except some last layers which are specific for the tasks. This type of multi-task learning can reduce the inference time. The soft parameter sharing represents the structure when each task has its own branch and between each branch, there is a connection to exchange information.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the following description, numerous specific details are given to provide a thorough understanding of the invention. However, it will be apparent that the invention may be practiced without these specific details. In order to avoid obscuring an embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for case of description generally show similar orientations, this depiction in the figures is arbitrary for the most part. Generally, the invention can be operated in any orientation. The embodiments of various components as a matter of descriptive convenience and are not intended to have any other significance or provide limitations for an embodiment of the present invention.

The term "module" or "unit" or "circuit" referred to herein can include or be implemented as or include software running on specialized hardware, hardware, or a combination thereof in the present invention in accordance with the context in which the term is used. For example, the software can be machine code, firmware, embedded code, and application software. The software can also include a function, a call to a function, a code block, or a combination thereof.

Also, for example, the hardware can be gates, circuitry, processor, computer, integrated circuit, integrated circuit cores, memory devices, a pressure sensor, an inertial sensor, a microelectromechanical system (MEMS), passive devices, physical non-transitory memory medium including instructions for performing the software function, a portion therein, or a combination thereof to control one or more of the hardware units or circuits. Further, if a "module" or "unit" or a "circuit" is written in the claims section below, the "unit" or the "circuit" is deemed to include hardware circuitry for the purposes and the scope of the claims.

The module, units, or circuits in the following description of the embodiments can be coupled or attached to one another as described or as shown. The coupling or attachment can be direct or indirect without or with intervening items between coupled or attached modules or units or circuits. The coupling or attachment can be by physical contact or by communication between modules or units or circuits, such as wireless communication.

It is also understood that the nouns or elements in the embodiments can be described as a singular instance. It is understood that the usage of singular is not limited to singular but the singular usage can be applicable to multiple instances for any particular noun or element in the application. The numerous instances can be the same or similar or can be different.

Referring now to FIG. 1, therein is shown an example of a system architecture diagram of a compute system 100 with a head ailment diagnostic mechanism in an embodiment of the present invention. Embodiments of the compute system 100 provide standardized and objective Alopecia scoring to provide for a reproducible precise SALT calculation.

The compute system 100 can include a first device 102, such as a client or a server, connected to a second device 106, such as a client or server. The first device 102 can communicate with the second device 106 through a network 104, such as a wireless or wired network.

For example, the first device 102 can be of any of a variety of computing devices, such as a smart phone, a tablet, a cellular phone, personal digital assistant, a notebook computer, a wearable device, internet of things (IoT) device, or other multi-functional device. Also, for example, the first device 102 can be included in a device or a sub-system.

The first device 102 can couple, either directly or indirectly, to the network 104 to communicate with the second device 106 or can be a stand-alone device. The first device 102 can further be separate form or incorporated with a smart phone, a tablet computer, a laptop computer, a scanner, or other personal electronic devices.

For illustrative purposes, the compute system 100 is described with the first device 102 as a mobile device, although it is understood that the first device 102 can be different types of devices. For example, the first device 102 can also be a non-mobile computing device, such as a server, a server farm, cloud computing, or a desktop computer.

The second device 106 can be any of a variety of centralized or decentralized computing devices. For example, the second device 106 can be a computer, grid computing resources, a virtualized computer resource, cloud computing resource, routers, switches, peer-to-peer distributed computing devices, or a combination thereof.

The second device 106 can be centralized in a single room, distributed across different rooms, distributed across different geographical locations, embedded within a telecommunications network. The second device 106 can couple with the network 104 to communicate with the first device 102. The second device 106 can also be a client type device as described for the first device 102.

For illustrative purposes, the compute system 100 is described with the second device 106 as a non-mobile computing device, although it is understood that the second device 106 can be different types of computing devices. For example, the second device 106 can also be a mobile computing device, such as notebook computer, another client device, a wearable device, or a different type of client device.

Also, for illustrative purposes, the compute system 100 is described with the second device 106 as a computing device, although it is understood that the second device 106 can be different types of devices. Also, for illustrative purposes, the compute system 100 is shown with the second device 106 and the first device 102 as endpoints of the network 104, although it is understood that the compute system 100 can include a different partition between the first device 102, the second device 106, and the network 104. For example, the first device 102, the second device 106, or a combination thereof can also function as part of the network 104.

The network 104 can span and represent a variety of networks. For example, the network 104 can include wireless communication, wired communication, optical, ultrasonic, or the combination thereof. Satellite communication, cellular communication, Bluetooth, Infrared Data Association standard (IrDA), wireless fidelity (WiFi), and worldwide interoperability for microwave access (WiMAX) are examples of wireless communication that can be included in the communication path. Ethernet, digital subscriber line (DSL), fiber to the home (FTTH), and plain old telephone service (POTS) are examples of wired communication that can be included in the network 104. Further, the network 104 can traverse a number of network topologies and distances. For example, the network 104 can include direct connection, personal area network (PAN), local area network (LAN), metropolitan area network (MAN), wide area network (WAN), or a combination thereof.

Returning to the description standardized and objective SALT scoring of the embodiments of the compute system 100, as an example, the compute system 100 provide functions to various patients 112, including patients and clinicians. The compute system 100 can provide functions to the patients 112 in a number of ways.

For example, the compute system 100 can provide the functions for the patients 112 with the first device 102, the second device 106, distributed between these two devices, or a combination thereof. Also as examples, the compute system 100 can provide mobile applications for the patients, the clinicians, or a combination thereof. Further as an example, the compute system 100 can provide the functions via a web-browser based applications or a software to be executed on the first device 102, the second device 106, distributed between these two devices, or a combination thereof.

In one embodiment as an example, patient images 114 are taken and uploaded by the patient and reviewed by the clinician. In this embodiment, a patient launches the head ailment diagnostic mechanism via the mobile application and logs into the patient's account. The patient can be prompted to upload or take images as the patient images 114. The compute system 100 can guide a patient 112 on photo guidelines for the patient images 114 and accepts or rejects the patient images 114 for retake based on pre-specified criteria, e.g., distance, quality, blur, or a combination thereof. The compute system 100 can also provide guides for a patient on capturing videos as opposed to still photos. The patient images 114 can be selected from the video.

Once the patient images 114, as required for analysis, are successfully uploaded, the compute system 100 can send or load the patient images 114 to a head ailment diagnostic module 115 for analysis. The head ailment diagnostic module 115 will be described later. For brevity and clarity and as an example, the head ailment diagnostic module 115 is shown as being executed in the second device 106 although it is understood that portions can operate on the first device 102, such as the mobile app or the web-browser based application, can operate completely on the first device 102, or a combination thereof. As a further example, the head ailment diagnostic module 115 can include a scalp segmentation module 118, a hair loss heat map module 120, and a severity of alopecia tool (SALT) score 122. The head ailment diagnostic module 115 can be implemented in software running on specialized hardware, full hardware, or a combination thereof. The head ailment diagnostic module 115 can be based on a multi-task convolutional neural network in a U-Net configuration.

The scalp segmentation module 118 can be implemented in software running on specialized hardware, full hardware, or a combination thereof. The scalp segmentation module 118 analyzes pixels in the patient images 114 to detect the areas of the scalp indicating hair loss. The scalp segmentation module 118 can complete the first task of the multi-tasking analysis engine.

The hair loss heat map module 120 can be implemented in software running on specialized hardware, full hardware, or a combination thereof. The hair loss heat map module 120 analyzes pixels in the patient images 114 to detect the intensity of hair loss in the patient images 114. The hair loss heat map module 120 can complete the second task of the multi-tasking analysis engine.

The SALT score 122 accounts for the percentage of hair loss based on pixel analysis in the patient images 114. The scalp segmentation module 118, and the hair loss heat map module 120 are combined to calculate the percentage of hair loss displayed in the patient images 114.

Based on analysis results, the compute system 100 can display information to the patient including a recommendation based on the patient images 114, uploaded, for the patient to schedule a visit with your primary care physician or with a specialist based on a scalp segmentation module 118 and the hair loss heat map module 120, which may or may not be visible or displayed to the patient.

Continuing the example, the compute system 100 can provide a function that allows the clinician to access the patient images 114 uploaded by the patient and the SALT score 122, such as with the web-based dashboard from the Alopecia diagnostic mechanism. The compute system 100 allows the clinician to make edits to annotations determined by the head ailment diagnostic module 115 and the scores (if necessary) and saves the results. The clinician can utilize the Scalp segmentation module 118 to make the diagnostic decision and takes necessary treatment steps (if applicable).

The compute system 100 can provide guidance to the clinician on the photo guidelines. The compute system 100 can accept or reject images for retake based on pre-specified criteria, such as distance, quality, blur, or a combination thereof. Once the patient images 114 are successfully uploaded, the compute system 100 and send or load the patient images 114 to the head ailment diagnostic module 115 for analysis.

Continuing the example, the compute system 100 can similarly provide a function that allow the clinician to access the patient images 114 uploaded by the patient 112 and the scalp segmentation module 118, such as with the web-based dashboard from the head ailment diagnostic mechanism. The compute system 100 allows the clinician to make edits to annotations determined by the head ailment diagnostic module 115 and the scores (if necessary) and saves the results. The clinician can utilize the SALT score 122 to make the diagnostic decision and takes necessary treatment steps (if applicable).

A quadrant computation module 124 can be coupled to the scalp segmentation module 118 in order to assist in the generation of a composite hair loss image 126 for presentation with the SALT score 122. The quadrant computation module 124 can be a software module executed on a specialized hardware platform. The quadrant computation module 124 can define regions within the patient images 114 that are used to compose the composite hair loss image 126.

It has been discovered that the compute system 100 can utilize multi-tasking U-Net convolutional neural network architecture for the head ailment diagnostic module 115 in order to reduce the inference time by running a single model to identify the scalp segmentation and the hair loss heat map. The compute system 100 can calculate the SALT score 122 based on the scalp segmentation and the hair loss heat map.

Figure 2:
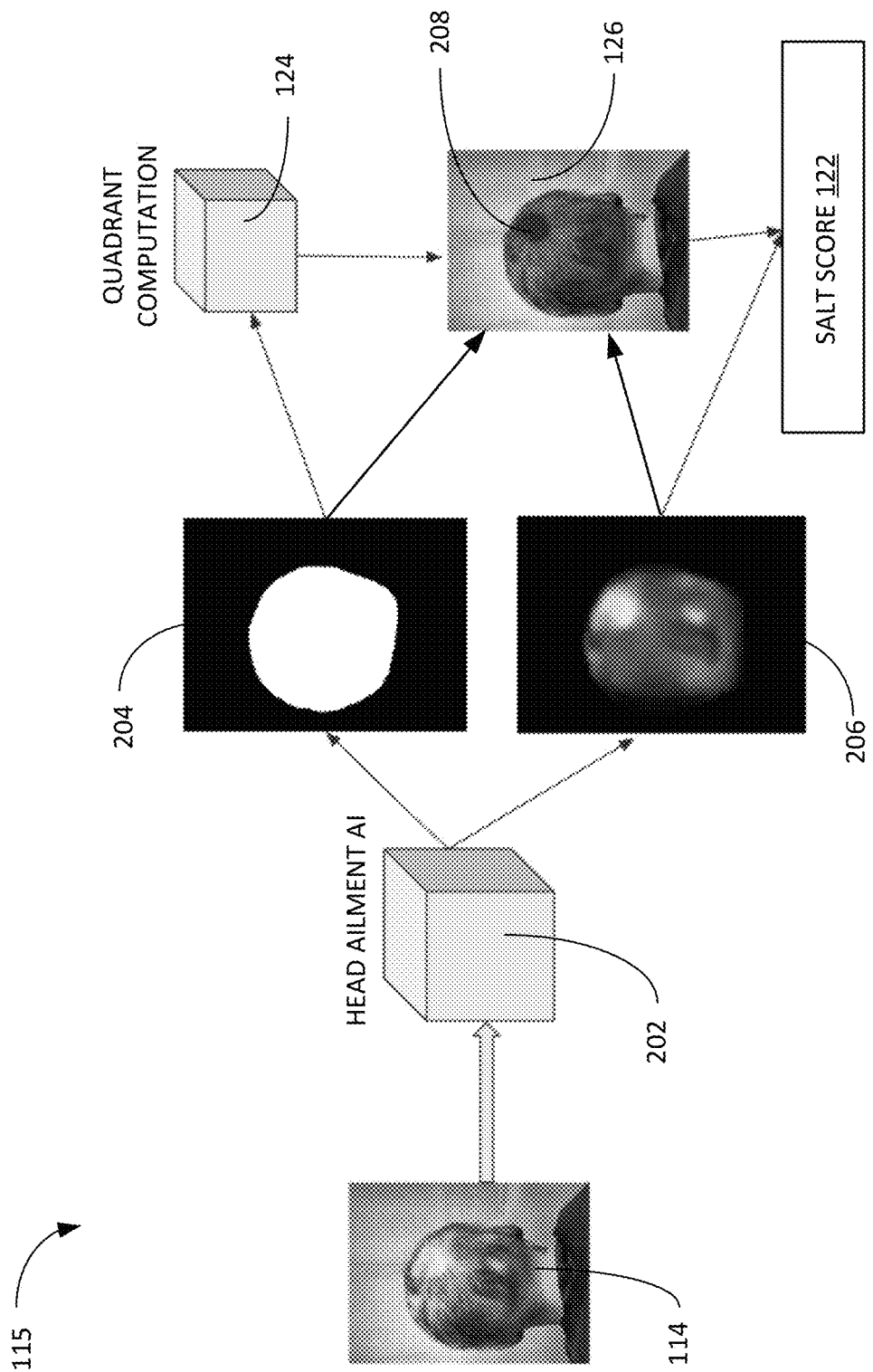
FIG. 2 is an example of a functional block diagram of the head ailment diagnostic module in an embodiment.

Referring now to FIG. 2, therein is shown a functional block diagram of the head ailment diagnostic module 115 in an embodiment. The functional block diagram of the head ailment diagnostic module 115 depicts the patient images 114 processed by the head ailment AI 202 to generate a scalp segmentation 204 and a hair loss heat map 206.

In this example, the head ailment diagnostic module 115 computes the SALT score 122 by analyzing four of the patient images 114 all of a person's head: left, right, top, and back. The head ailment diagnostic module 115 includes two parts. The first part operates the head ailment AI 202, such as a multi-tasking deep learning model, whose input is the patient image 114 and whose outputs are the scalp segmentation 204 and the hair loss heat map 206.

The hair loss heat map 206 shows the percentage of hair loss, the result of a regression task performed by the head ailment AI 202 on the patient image 114. The head ailment AI 202 uses a multi-task learning for this model because of the high correlation between the processes of detecting the scalp segmentation 204 and the hair loss heat map 206. This approach also reduces the inference time by half since only one model is executed instead of two separate models. The head ailment AI 202 provides an ICC of 0.97, as compared to a doctor's examination. It is understood that the ICC greater than 0.9 indicates excellent accuracy.

In the generation of the hair loss heat map 206, the percentage of hair loss for the whole head is computed based on the hair loss heat map module 120 processing four of the patient images 114, as an example. The system compiles the results of four of the patient images 114 and computes the SALT score 122 for the entirety of the head of the patient 112. The scalp segmentation 204 can identify the region of interest to be submitted to the quadrant computation module 124 in order to identify quadrants on each of the patient images 114. The quadrants within each of the patient images 114 are analyzed to find the extreme points of the scalp contour; then identify parabolas which pass through those points; and finally, connect all the parabolas to obtain a completed quadrant.

The quadrants defined by the quadrant computation module 124 can be combined with the hair loss heat map 206 can provide a pixel-by-pixel analysis in order to generate the composite hair loss image 126. The composite hair loss image 126 can be similar to the patient images 114 with hair loss markers 208 that identify the location and severity of hair loss in each of the patient images 114. The combination of the hair loss heat map 206 and the composite hair loss image 126 are used to calculate the SALT score 122 for each of the quadrants identified by the quadrant computation module 124.

It has been discovered that the head ailment diagnostic module 115 can analyze the patient images 114 through the multi-task analysis of the head ailment AI 202 to generate the scalp segmentation 204 and the hair loss heat map 206. The head ailment diagnostic module 115 combines the scalp segmentation 204 and the hair loss heat map 206 can be used to calculate the SALT score 122 to provide the patient 112 with a display of the composite hair loss image 126 and the percentage of hair loss determined by the SALT score 122.

Figure 3:
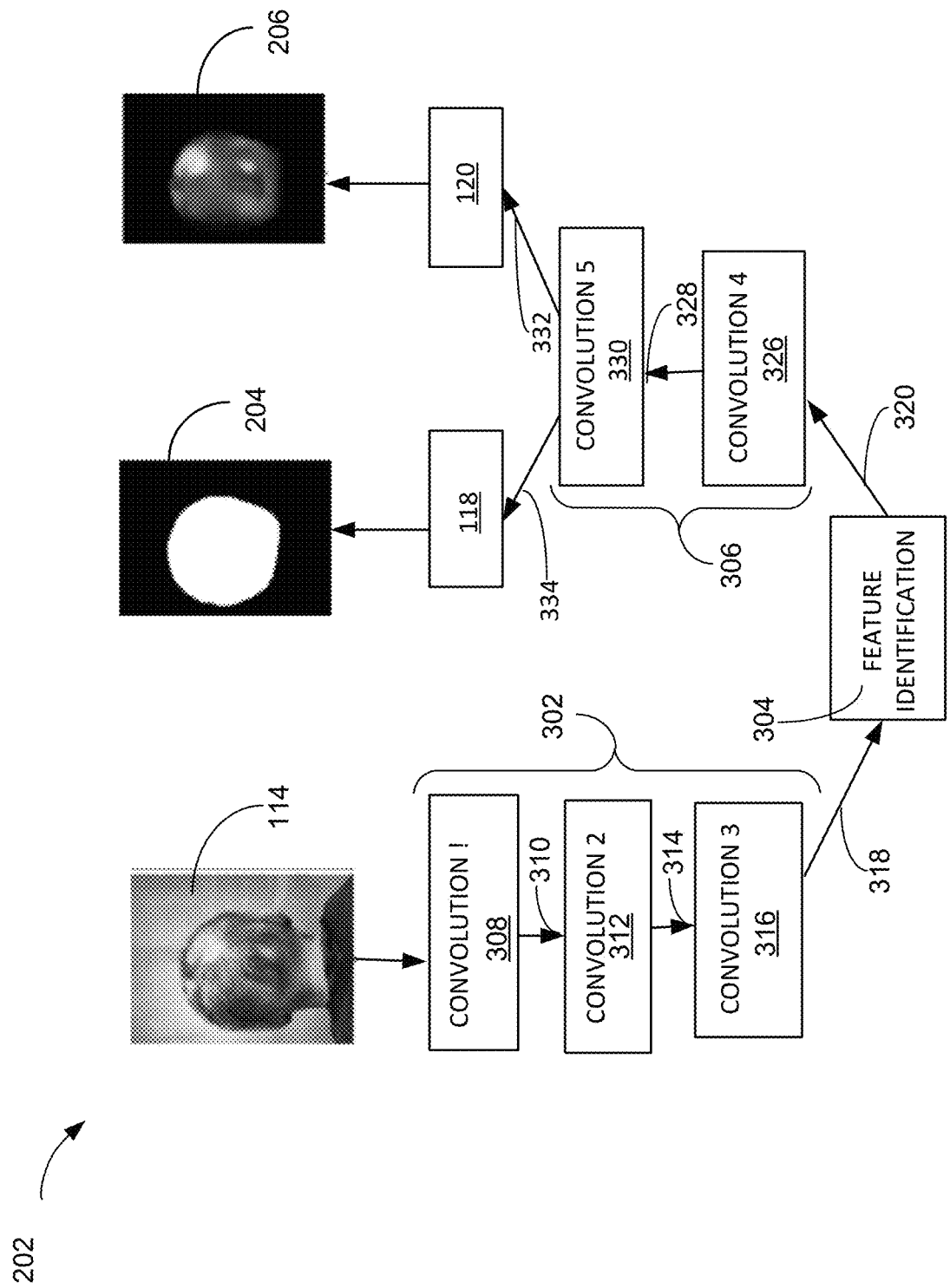
FIG. 3 is an example of a detailed functional block diagram of the head ailment AI in an embodiment.

Referring now to FIG. 3, therein is shown a functional block diagram of the head ailment AI 202 in an embodiment. As a specific example, FIG. 3 can depict a U-net implementation of the head ailment AI 202. The head ailment AI 202 computes the SALT score 122 of FIG. 1, a hair loss heat map module 120, and scalp segmentation module 118 for processing the patient images 114 uploaded for the patient 112.

The head ailment AI 202 can process the patient images 114, each of which can covers a specific part of the head from different angles of the head shown in the patient images 114 to cover the full surface of the head of the patient 112 to be analyzed. As a specific example, the head ailment AI 202 can process four (4) images that cover the full head of the patient 112. In this example, the patient images 114 cover a left side, a right side, a back, and a top of head. The compute system 100, the head ailment AI 202, or a combination thereof can compute the SALT score 122 if there are four (4) images for the patient 112.

In this example for an embodiment, the head ailment AI 202 can preprocess the patient images 114 to determine if each of the patient images 114 should proceed to be utilized to compute the SALT score 122. The head ailment AI 202 can include an encoder block 302, a feature identification block 304, and a multi-task decoder block 306. The patient images 114 can be submitted to the encoder block 302 for pixel analysis. The encoder block 302 can include a first convolution module 308 to generate an initial segmentation 310 of the pixels in the patient images 114.

The output of the first convolution module 308 can be coupled to a second convolution module 312, which applies weighted filters to the initial segmentation 310 in order to produce a further segmentation 314. The further segmentation 314 reduces the special dimensions to differentiate the pixels for processing by a third convolution module 316. The third convolution module 316 can apply a finer set of the weighted filter to enhance a pixel group 318 for analysis by the feature identification block 304.

The feature identification block 304 has been trained to concurrently identify the areas of scalp and areas of reduced density of hair within the areas of scalp. The analysis by the feature identification block 304 is performed on a pixel-by-pixel basis. The feature identification block 304 can identify a hair loss factor 320 providing a scalp label and a heatmap label that can differentiate four levels of hair loss within the segmented scalp area. They are normal hair with 0% hair loss, a first stage hair loss of 1-33% hair loss, a second stage hair loss of 34-66% hair loss, and a final stage hair loss with 67-100% hair loss.

The hair loss factor 320 providing the scalp label and the heatmap label can be processed through the multi-task decoder block 306 to concurrently develop a scalp segmentation 204 and a hair loss heat map 206. The feature identification block 304 can be coupled to a fourth convolution module 326 in order to reconstruct the segmented information of the hair loss factor 320 by applying weighted filters to create larger segments of a converged data stream 328. The converged data stream 328 provides larger segments of the pixel group 318 with features identified for both the Scalp segmentation module 118 and the hair loss heat map module 120. The concurrent identification and analysis of the scalp segmentation 204 and the hair loss heat map 206 can increase the confidence level and accuracy of the analysis, while reducing the time required to develop the composite image 126 of FIG. 1 and the SALT score 122.

The converged data stream 328 can be further processed and converged by a fifth convolutional module 330. The fifth convolutional module 330 concurrently deliver a heat map stream 332 and a scalp segmentation stream 334 in the processing of the multi-task decoder block 306. The heat map stream 332 can be processed by the hair loss heat map module 120 in order to produce the hair loss heat map 206. The scalp segmentation stream 334 can be processed by the Scalp segmentation module 118 in order to produce the scalp segmentation 204.

The Scalp segmentation module 118 and the hair loss heat map module 120 can provide information to calculate the SALT score 122. The head ailment AI 202 processes multi-task functions in order to produce the scalp segmentation 204, the hair loss heat map 206, and the SALT score 122 for presentation to a clinician or the patient 112.

It has been discovered that the head ailment AI 202 can process the patient images 114 in the multi-tasking flow of the head ailment AI 202. The head ailment diagnostic module can identify the condition captured in the patient images 114 to determine the normal hair, the first stage hair loss, a second stage hair loss, and a final stage hair loss. The SALT score 122 can indicate the seriousness and percentage of hair loss caused by the Alopecia.

Figure 4:
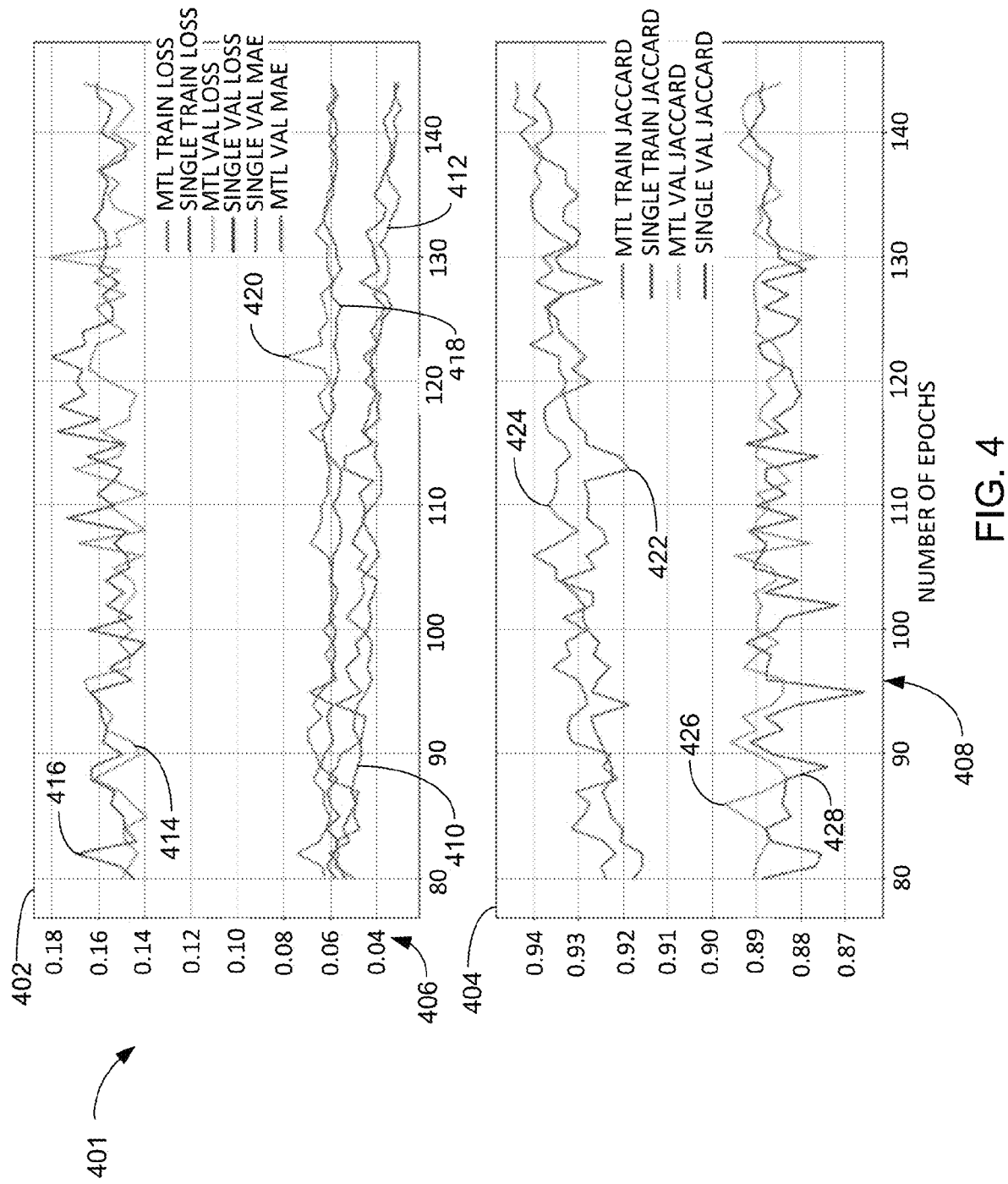
FIG. 4 is a training and validation graphs for the head ailment AI in an embodiment.

Referring now to FIG. 4, therein is shown a training and validation graphs 401 for the head ailment AI 202 in an embodiment. The training and validation graphs 401 for the head ailment AI 202 depicts a loss graph 402 and a Jaccard score graph 404.

The loss graph 402 can demonstrate loss functions for both a multi-tasking learning structure, such as the head ailment AI 202, and a single task learning AI for both training and validation. A loss scale 406, on a vertical axis, can range from 0.04 through 0.18 indicating the difference between the model's predicted output and the actual values of the data being evaluated. An epochs scale 408, on a horizontal scale, represents the number of times a training dataset passes through a learning algorithm. A multi-task training loss 410 (in blue) is compared to a single task training loss 412 (in green). Both the multi-task training loss 410 and the single task training loss 412 decrease with the increase in the number of the epochs scale 408. At 145 epochs, the multi-task training loss 410 and the single task training loss 412 are approximately equal.

A multi-task validation loss 414 (in orange) is compared to the single task validation loss 416 (in red). Both the multi-task validation loss 414 and the single task validation loss 416 remain relatively consistent across the validation process. While the validation loss of the multi-task validation loss 414 and the single task validation loss 416 are similar, the single task validation loss 416 must be run twice to accomplish the two tasks that are accomplished by a single run of the multi-task validation loss 414.

A multi-task validation mean average error (mac) 418 (in gray) is compared to a single task validation mac 420 (in violet). The multi-task validation mac 418 remains lower than the single task validation mae 420 across the validation process. The multi-task process of the head ailment AI 202 demonstrates better accuracy and has a two-to-one time advantage.

The Jaccard score graph 404 depicts a multi-task training jaccard score 422 (in blue) compared to a single task training jaccard score 424 (in green). The higher value of the jaccard score means better matching of predicted values and actual values. The jaccard score operates on a scale of 1 to 0, where 1 is complete correlation and 0 means no correlation. A multi-task validation jaccard score 426 (in orange) is compared to a single task validation jaccard 428 (in red). While the values of the multi-task validation jaccard score 426 and the single task validation jaccard 428 are similar, the multi-task validation jaccard score 426 is higher on average. Jaccard score is utilized as expressed in Equation 1 and graphed in this figure.

$$J(A,B)=(|A \cap B|)/(|A \cup B|) \qquad \text{Equation 1}$$

Where A is the training data set and B is the validation data set. The Jaccard score, also known as the Jaccard similarity coefficient, is a statistic used for gauging the similarity and diversity of sample sets. Equation 1 can be used to measure the similarity between finite sample sets, it is defined as the ratio of the intersection over the union of the two sets.

It has been discovered that the head ailment AI 202, demonstrating the multi-task validation loss 414, the multi-task validation mac 418, and the multi-task validation jaccard score 426, provides accuracy with the multi-task validation mac 418 of 0.06 and multi-task validation jaccard score 426 of 0.89. While demonstrating accuracy of the analysis of the scalp segmentation 204 of FIG. 2 and the hair loss heat map 206 of FIG. 2, the head ailment AI 202 reduces the inference time and gives consistent and accurate results over the single task AI known in the industry.

Figure 5:
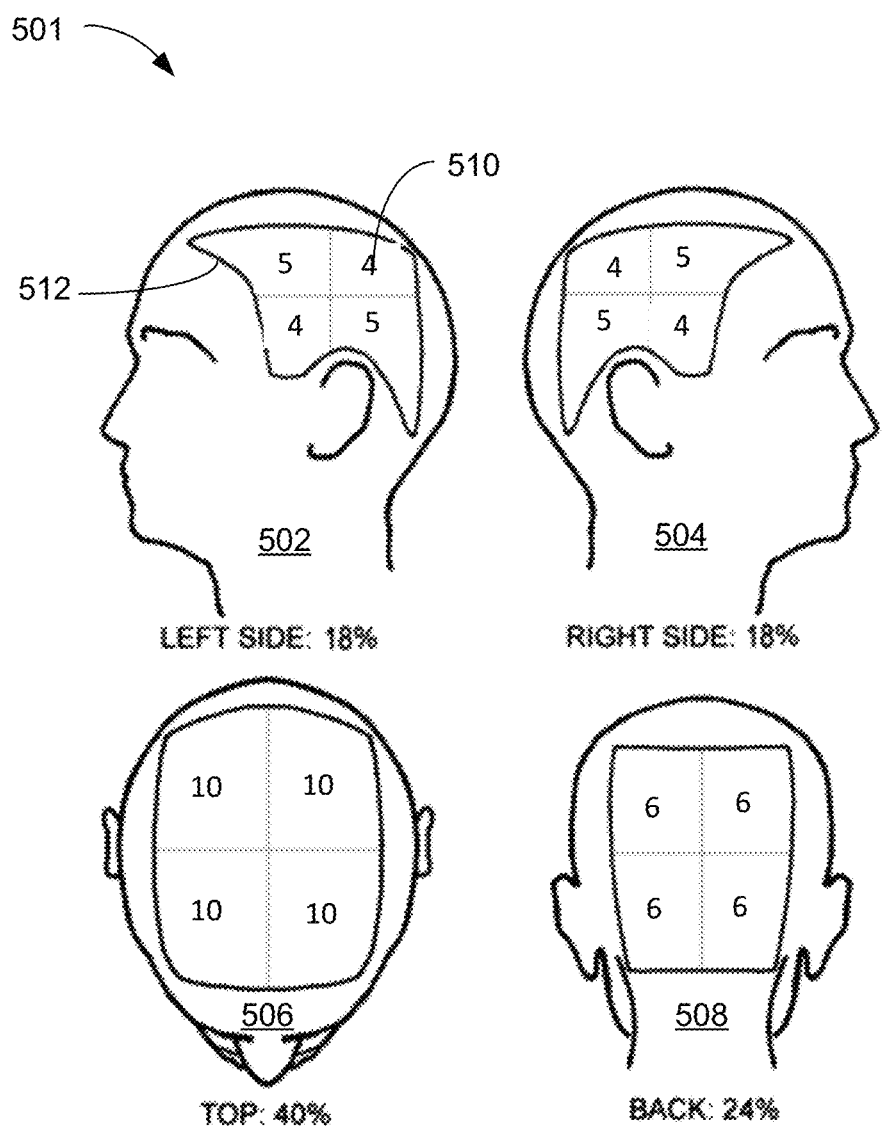
FIG. 5 is an exemplary diagram of the patient image with a weighted sum of percentages of hair loss for each quadrant.

Referring now to FIG. 5, therein is shown an exemplary diagram 501 of the patient images 114 with a weighted sum of percentages of hair loss for each quadrant. The exemplary diagram 501 of the patient images 114 depicts a left side image 502, a right side image 504, a top image 506, and a back image 508. Each of the patient images 114 represents a weighted percentage 510 of a scalp area 512.

By way of an example the weighted percentages 510 can reflect, the left side image 502 can represent 18% of the scalp area 512, the right side image 504 can represent 18% of the scalp area 512, the top image 506 can represent 40% of the scalp area 512, and the back image 508 can represent 24% of the scalp area 512. The head ailment AI 202 of FIG. 1 can automatically calculate the SALT score 122 of FIG. 1 based on the weighted percentages 510 of the hair loss factor 320 of FIG. 2 identified in the scalp area 512.

The head ailment AI 202 performs a pixel-by-pixel analysis of the patient images 114 in order to deliver the SALT score 122 by totaling the weighted percentages 510 of the hair loss factor 320 in the left side image 502, the right side image 504, the top image 506, and the back image 508. It is understood that the hair loss heat map module 120 of FIG. 1 can identify some areas of hair loss extends across the borders of the left side image 502, the right side image 504, the top image 506, and the back image 508. The SALT score 122 takes into consideration the percent of hair loss represented in all of the patient images 114.

Figure 6:
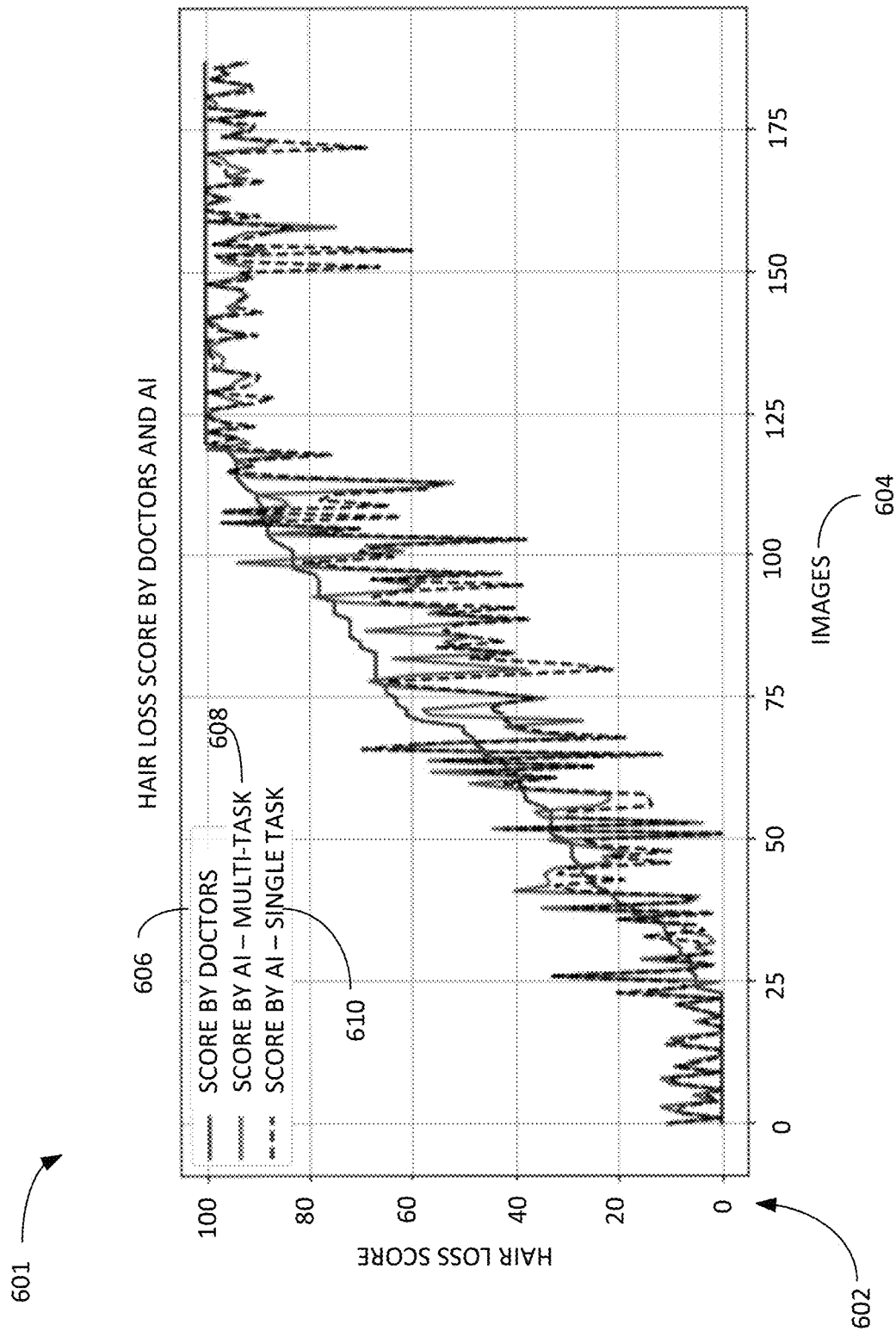
FIG. 6 is an example of a capability comparison graph of hair loss score identified by doctors and the head ailment diagnostic module in an embodiment.

Referring now to FIG. 6, there in is shown an example of a capability comparison graph 601 of hair loss score 602 identified by doctors and the head ailment diagnostic module 115 of FIG. 1 in an embodiment. The capability comparison graph 601 depicts the results of testing with 188 images 604 representing 47 sets of the patient images 114 with the left side image 502 of FIG. 5, the right side image 504 of FIG. 5, the top image 506 of FIG. 5, and the back image 508 of FIG. 5 for each patient 112 of FIG. 1. The patient images 114 were photographs taken during clinic visits using an iPad. Each of the patient images 114 was independently scored by a doctor (a veteran U.S. dermatologist) and by the head ailment diagnostic module 115 system, with the score representing the percentage of the hair loss 602 in that image.

The capability comparison graph 601 depicts a score by doctors 606 shown in blue, which is regarded as the standard for the capability comparison graph 601. The capability comparison graph 601 shows an increasing hair loss score 602 found in the individual images without grouping as the patient images 114. This was done to more easily identify the capabilities of the head ailment AI 202.

The head ailment diagnostic module 115 was generated by the head ailment AI 202, implemented as the multi-task AI, providing scores by AI-multi-task 608, shown in red, and a single task AI providing scores by AI-single task 610, shown in black dash lines. Each version of the head ailment AI 202 was trained with 145 epochs with a step per epoch of 200 and a batch size of 20. The single task AI requires additional processing to determine the hair loss score 602, while the multi-task AI delivers the hair loss score 602 in the initial pass.

The score by doctors 606 was compared to the head ailment diagnostic module 115, both single task and multi-task versions of the head ailment AI 202, using intraclass correlation coefficient (ICC) to measure accuracy. It can be noted that, based on a 95% confidence interval, ICC scores less than 0.5 indicate poor correlation, scores between 0.5 and 0.75 indicate fair correlation, scores between 0.75 and 0.9 indicate good correlation, and scores greater than 0.90 indicate excellent accuracy.

The scores by AI-single task 610 demonstrated an ICC of 0.95 for the SALT scores 122 of FIG. 1, which are composed of the total percentage of hair loss in the set of the patient images 114. The left side image 502 had an ICC score of 0.91, the right side image 504 had an ICC score of 0.93, the top image 506 had an ICC score of 0.93, and the back image 508 had an ICC score of 0.91.

The scores by AI-multi-task 608 demonstrated an ICC of 0.95 for the SALT scores 122, but had higher ICC scores for the quadrants of the patient images 114. The left side image 502 had an ICC score of 0.96, the right side image 504 had an ICC score of 0.97, the top image 506 had an ICC score of 0.95, and the back image 508 had an ICC score of 0.92.

As demonstrated by the capability comparison graph 601 the head ailment AI 202 performs well in providing the hair loss score 602 with the ICC of 0.95 as compared to the score by doctors 606. The scores by AI-multi-task 608, as provided by the head ailment diagnostic module 115 provides excellent accuracy with the ICC of 0.95 with a single operation of evaluating the patient images 114 to provide both the scalp segmentation 204 of FIG. 2 and the hair loss heat map 206 of FIG. 2 as well as the SALT score 122 in a single operation.

Figure 7:
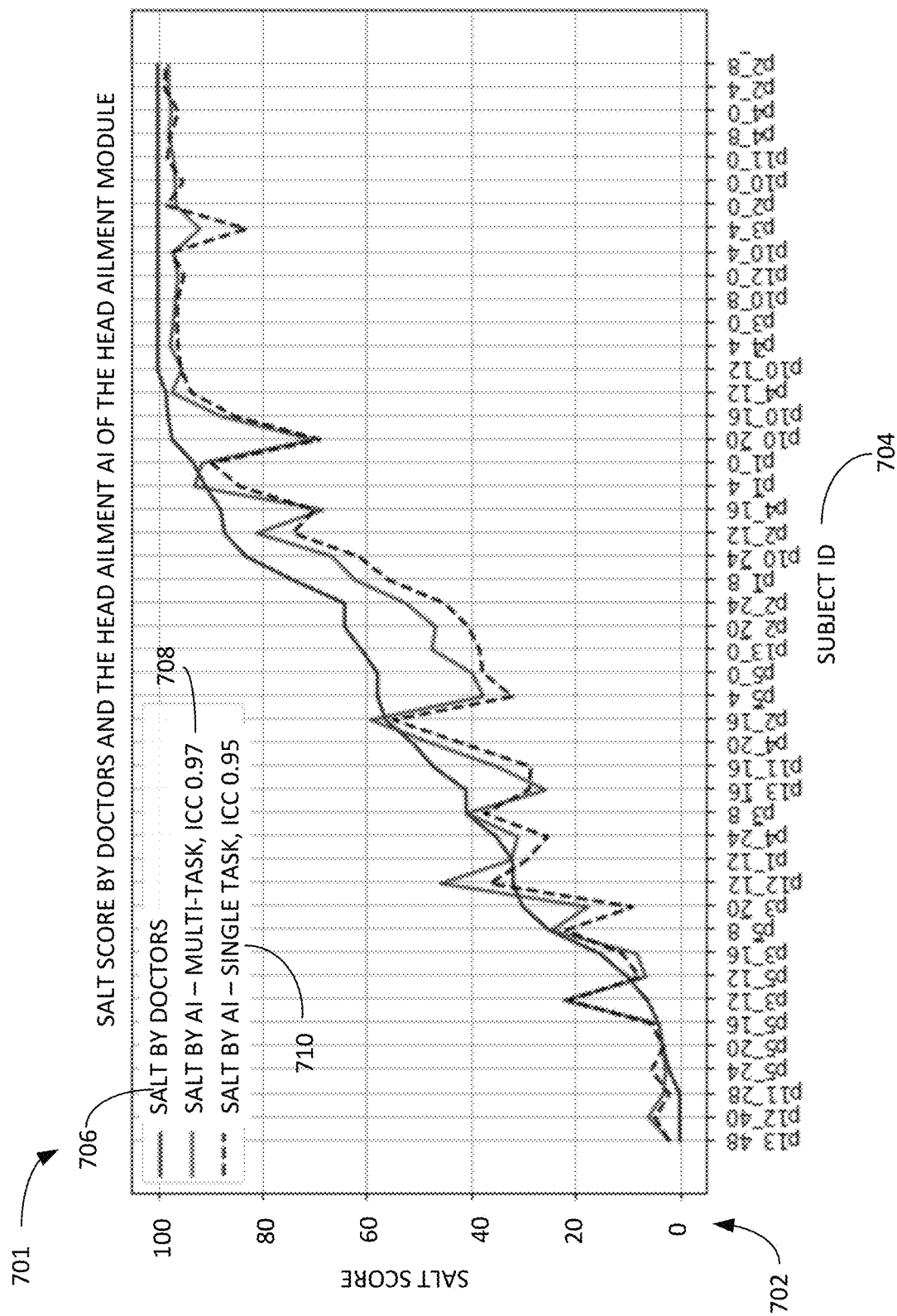
FIG. 7 is an example of a SALT comparison graph of SALT scores identified by doctors and the head ailment diagnostic module in an embodiment.

Referring now to FIG. 7, therein is shown an example of a SALT comparison graph 701 of SALT scores 702 identified by doctors and the head ailment diagnostic module 115 of FIG. 1 in an embodiment. The SALT comparison graph 701 depicts the results of testing with 188 images 604 representing 47 sets of the patient images 114 of FIG. 1 for each patient 112 of FIG. 1. A subject ID 704 can be assigned to each of the patient 112 of FIG. 1 used in the SALT comparison graph 701. Each of the patient images 114 was independently scored by a doctor (a veteran U.S. dermatologist) and by the head ailment diagnostic module 115 system, with the score representing the SALT score 702 for each of the patient 112 represented by the subject ID 704.

The SALT comparison graph 701 depicts a SALT by doctors 706, shown in blue, which is regarded as the standard for the SALT comparison graph 701. The SALT comparison graph 701 shows an increasing SALT score 702 found in the individual images of the patient images 114. This was done to more easily identify the capabilities of the head ailment diagnostic module 115.

The head ailment diagnostic module 115 includes the head ailment AI 202 of FIG. 2 was generated as the multi-task AI providing SALT by AI-multi-task 708, shown in red, and a single task AI providing SALT by AI-single task 710, shown in black dash lines. Each version of the head ailment AI 202 was trained with 145 epochs with a step per epoch of 200 and a batch size of 20. The single task AI requires additional processing to determine the SALT score 702, while the multi-task AI delivers the SALT score 702 in the initial pass.

The SALT by doctors 706 was compared to the head ailment AI 202, both the SALT by AI-single task 710 and the SALT by AI-multi-task 708, using intraclass correlation coefficient (ICC) to measure accuracy. It can be noted that, based on a 95% confidence interval, ICC scores less than 0.5 indicate poor correlation, scores between 0.5 and 0.75 indicate fair correlation, scores between 0.75 and 0.9 indicate good correlation, and scores greater than 0.90 indicate excellent accuracy.

The SALT by AI-single task 710 demonstrated an ICC of 0.95 for the SALT score 702, which are composed of the total percentage of hair loss in the set of the patient images 114 for each of the subject id 704. The SALT by AI-multi-task 708 demonstrated an ICC of 0.97 for the SALT scores 702 of the patient images 114.

The SALT by AI-multi-task 708, as provided by the head ailment AI 202 provides excellent accuracy with the ICC of 0.97 with a single operation of evaluating the patient images 114 to provide both the scalp segmentation 204 of FIG. 2 and the hair loss heat map 206 of FIG. 2 as well as the SALT score 702 in a single operation. The generation of the SALT score 702 automatically by the head ailment AI 202 simplifies the task, which requires multiple steps performed by the Doctor analyzing the patient images 114.

Figure 8:
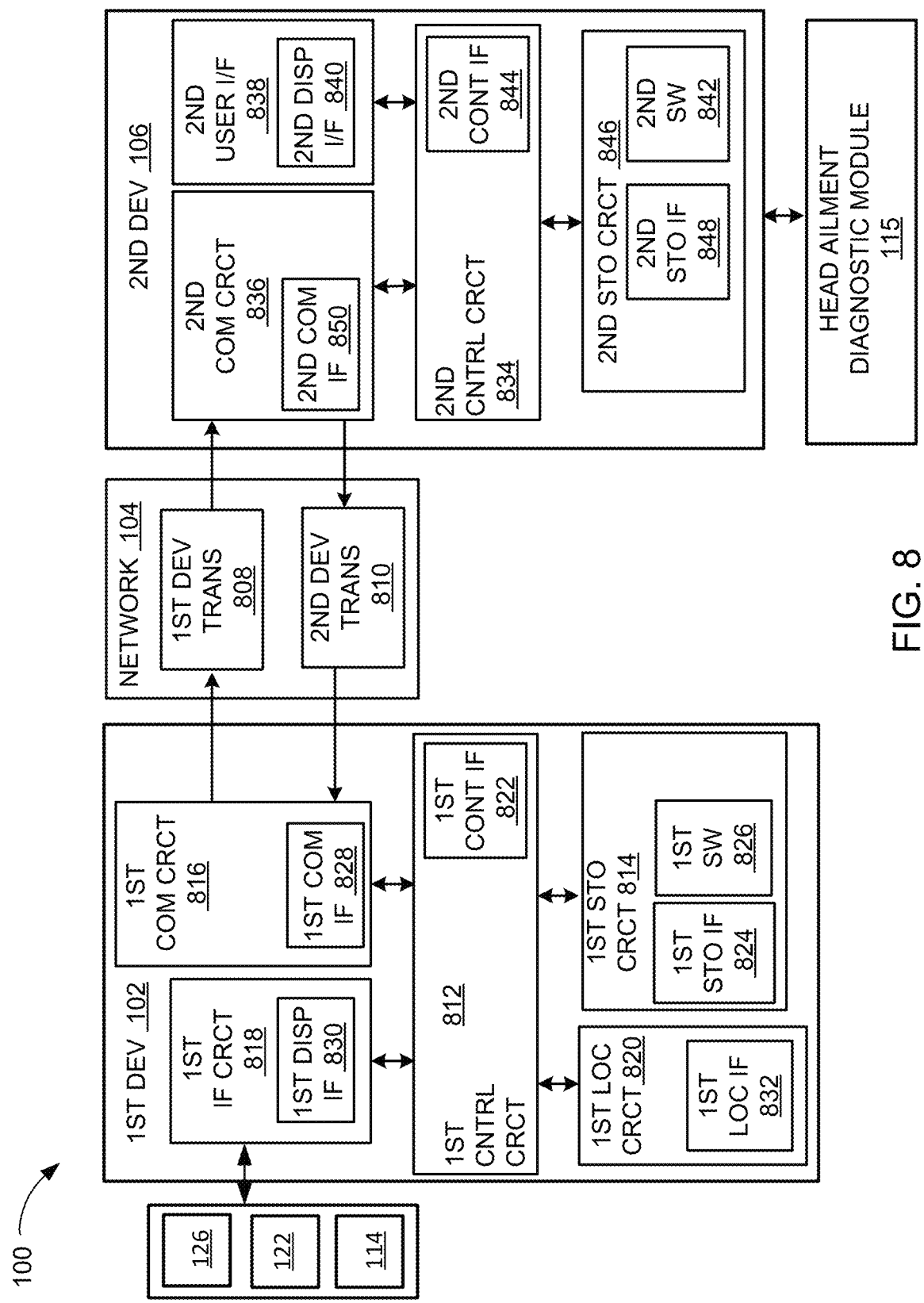
FIG. 8 is an exemplary block diagram of the compute system in an embodiment.

Referring now to FIG. 8, therein is shown an exemplary block diagram of the compute system 100 in an embodiment. The compute system 100 can include the first device 102, the network 104, and the second device 106. The first device 102 can send information in a first device transmission 808 over the network 104 to the second device 106. The second device 106 can send information in a second device transmission 810 over the network 104 to the first device 102.

For illustrative purposes, the compute system 100 is shown with the first device 102 as a client device, although it is understood that the compute system 100 can include the first device 102 as a different type of device.

Also, for illustrative purposes, the compute system 100 is shown with the second device 106 as a server, although it is understood that the compute system 100 can include the second device 106 as a different type of device. For example, the second device 106 can be a client device. By way of an example, the compute system 100 can be implemented entirely on the first device 102 with some functions of the head ailment diagnostic module 115 executed by a first control circuit 812.

Also, for illustrative purposes, the compute system 100 is shown with interaction between the first device 102 and the second device 106. However, it is understood that the first device 102 can be a part of or the entirety of a tablet computer, a smart phone, or a combination thereof. Similarly, the second device 106 can similarly interact with the first device 102 representing the tablet computer, the smart phone, or a combination thereof.

For brevity of description in this embodiment of the present invention, the first device 102 will be described as a client device and the second device 106 will be described as a server device. The embodiment of the present invention is not limited to this selection for the type of devices. The selection is an example of an embodiment of the present invention.

The first device 102 can include the first control circuit 812, a first storage circuit 814, a first communication circuit 816, a first interface circuit 818, and a first location circuit 820. The first control circuit 812 can include a first control interface 822. The first control circuit 812 can execute a first software 826 to provide the intelligence of the compute system 100.

The first control circuit 812 can be implemented in a number of different manners. For example, the first control circuit 812 can be a processor, an application specific integrated circuit (ASIC), an embedded processor, a microprocessor, a hardware control logic, a hardware finite state machine (FSM), a digital signal processor (DSP), or a combination thereof. The first control interface 822 can be used for communication between the first control circuit 812 and other functional units or circuits in the first device 102. The first control interface 822 can also be used for communication that is external to the first device 102. The first control circuit 812 can process the patient images 114 and execute portions of the head ailment diagnostic module 115.

The first control interface 822 can receive information from the other functional units/circuits or from external sources or can transmit information to the other functional units/circuits or to external destinations. The external sources and the external destinations refer to sources and destinations external to the first device 102.

The first control interface 822 can be implemented in different ways and can include different implementations depending on which functional units/circuits or external units/circuits are being interfaced with the first control interface 822. For example, the first control interface 822 can be implemented with a pressure sensor, an inertial sensor, a microelectromechanical system (MEMS), optical circuitry, waveguides, wireless circuitry, wireline circuitry, or a combination thereof.

The first storage circuit 814 can store the first software 826. The first storage circuit 814 can also store the relevant information, such as data representing incoming patient images 114, data representing the scalp segmentation 204 of FIG. 2, the hair loss heat map 206 of FIG. 2, the composite hair loss image 126, the SALT scores 122, or a combination thereof.

The first storage circuit 814 can be a volatile memory, a nonvolatile memory, an internal memory, an external memory, or a combination thereof. For example, the first storage circuit 814 can be a nonvolatile storage such as non-volatile random-access memory (NVRAM), Flash memory, disk storage, or a volatile storage such as static random-access memory (SRAM).

The first storage circuit 814 can include a first storage interface 824. The first storage interface 824 can be used for communication between the first storage circuit 814 and other functional units or circuits in the first device 102. The first storage interface 824 can also be used for communication that is external to the first device 102.

The first storage interface 824 can receive information from the other functional units/circuits or from external sources or can transmit information to the other functional units/circuits or to external destinations. The external sources and the external destinations refer to sources and destinations external to the first device 102. The first storage interface 824 can receive input from and source data to the head ailment diagnostic module 115.

The first storage interface 824 can include different implementations depending on which functional units/circuits or external units/circuits are being interfaced with the first storage circuit 814. The first storage interface 824 can be implemented with technologies and techniques similar to the implementation of the first control interface 822.

The first communication circuit 816 can enable external communication to and from the first device 102. For example, the first communication circuit 816 can permit the first device 102 to communicate with the second device 106 and the network 104. The first communication circuit 816 can interact with the second device 106 for implementing the head ailment diagnostic module 115.

The first communication circuit 816 can also function as a communication hub allowing the first device 102 to function as part of the network 104 and not limited to be an endpoint or terminal circuit to the network 104. The first communication circuit 816 can include active and passive components, such as microelectronics or an antenna, for interaction with the network 104.

The first communication circuit 816 can include a first communication interface 828. The first communication interface 828 can be used for communication between the first communication circuit 816 and other functional units or circuits in the first device 102. The first communication interface 828 can receive information from the second device 106 for distribution to the other functional units/circuits or can transmit information to the other functional units or circuits.

The first communication interface 828 can include different implementations depending on which functional units or circuits are being interfaced with the first communication circuit 88. The first communication interface 828 can be implemented with technologies and techniques similar to the implementation of the first control interface 822.

The first interface circuit 818 allows the patient 112 of FIG. 1 to interface and interact with the first device 102. The first interface circuit 818 can include an input device and an output device. Examples of the input device of the first interface circuit 818 can include a keypad, a touchpad, soft-keys, a keyboard, a microphone, a camera, an infrared sensor for receiving remote signals, or any combination thereof to provide data and communication inputs, such as the patient images 114. The first interface circuit 818 can receive the patient images 114 provided by the patient 112 that can be manipulated by the first control circuit 812.

The first interface circuit 818 can include a first display interface 830. The first display interface 830 can include an output device. The first display interface 830 can include a projector, a video screen, a touch screen, a speaker, a microphone, a keyboard, and combinations thereof. The first display interface 830 can allow the patient to view the composite hair loss image 126 and the SALT score 122 on the output device.

The first control circuit 812 can operate the first interface circuit 818 to display information generated by the compute system 100 and receive input from the patient 112. The first control circuit 812 can also execute the first software 826 for the other functions of the compute system 100, including receiving location information from the first location circuit 820. The first control circuit 812 can further execute the first software 826 for interaction with the network 104 via the first communication circuit 816. The first control circuit 812 can operate portions or all of the head ailment diagnostic module 115.

The first control circuit 812 can also receive location information from the first location circuit 820. The first control circuit 812 can operate the head ailment diagnostic module 115 or portions thereof. The first control circuit 812 can operate on the patient images 114, as well as preparing the composite hair loss image 126 and the SALT score 122 for display to the patient 112.

The first location circuit 820 can be implemented in many ways. For example, the first location circuit 820 can function as at least a part of the global positioning system, an inertial compute system, a cellular-tower location system, a gyroscope, or any combination thereof. Also, for example, the first location circuit 820 can utilize components such as an accelerometer, gyroscope, or global positioning system (GPS) receiver.

The first location circuit 820 can include a first location interface 832. The first location interface 832 can be used for communication between the first location circuit 820 and other functional units or circuits in the first device 102, including the environmental sensors 210.

The first location interface 832 can receive information from the other functional units/circuits or from external sources or can transmit information to the other functional units/circuits or to external destinations. The external sources and the external destinations refer to sources and destinations external to the first device 102. The first location interface 832 can receive the global positioning location from the global positioning system (not shown).

The first location interface 832 can include different implementations depending on which functional units/circuits or external units/circuits are being interfaced with the first location circuit 820. The first location interface 832 can be implemented with technologies and techniques similar to the implementation of the first control circuit 812.

The second device 106 can be optimized for implementing an embodiment of the present invention in a multiple device embodiment with the first device 102. The second device 106 can provide the additional or higher performance processing power compared to the first device 102. The second device 106 can include a second control circuit 834, a second communication circuit 836, a second user interface 838, and a second storage circuit 846.

The second user interface 838 allows an operator (not shown) to interface and interact with the second device 106. The second user interface 838 can include an input device and an output device. Examples of the input device of the second user interface 838 can include a keypad, a touchpad, soft-keys, a keyboard, a microphone, or any combination thereof to provide data and communication inputs. Examples of the output device of the second user interface 838 can include a second display interface 840. The second display interface 840 can include a display, a projector, a video screen, a speaker, or any combination thereof.

The second control circuit 834 can execute a second software 842 to provide the intelligence of the second device 106 of the compute system 100. The second software 842 can operate in conjunction with the first software 826. The second control circuit 834 can provide additional performance compared to the first control circuit 812. The second control circuit 834 can execute instructions to implement all or some of the functions of the head ailment diagnostic module 115.

The second control circuit 834 can operate the second user interface 838 to display information. The second control circuit 834 can also execute the second software 842 for the other functions of the compute system 100, including operating the second communication circuit 836 to communicate with the first device 102 over the network 104.

The second control circuit 834 can be implemented in a number of different manners. For example, the second control circuit 834 can be a processor, an embedded processor, a microprocessor, hardware control logic, a hardware finite state machine (FSM), a digital signal processor (DSP), or a combination thereof.

The second control circuit 834 can include a second control interface 844. The second control interface 844 can be used for communication between the second control circuit 834 and other functional units or circuits in the second device 106. The second control interface 844 can also be used for communication that is external to the second device 106.

The second control interface 844 can receive information from the other functional units/circuits or from external sources or can transmit information to the other functional units/circuits or to external destinations. The external sources and the external destinations refer to sources and destinations external to the second device 106.

The second control interface 844 can be implemented in different ways and can include different implementations depending on which functional units/circuits or external units/circuits are being interfaced with the second control interface 844. For example, the second control interface 844 can be implemented with a pressure sensor, an inertial sensor, a microelectromechanical system (MEMS), optical circuitry, waveguides, wireless circuitry, wireline circuitry, or a combination thereof.

The second storage circuit 846 can store the second software 842. The second storage circuit 846 can also store the information such as data representing incoming images, data representing previously presented image, sound files, or a combination thereof. The second storage circuit 846 can be sized to provide the additional storage capacity to supplement the first storage circuit 814.

For illustrative purposes, the second storage circuit 846 is shown as a single element, although it is understood that the second storage circuit 846 can be a distribution of storage elements. Also, for illustrative purposes, the compute system 100 is shown with the second storage circuit 846 as a single hierarchy storage system, although it is understood that the compute system 100 can include the second storage circuit 846 in a different configuration. For example, the second storage circuit 846 can be formed with different storage technologies forming a memory hierarchal system including different levels of caching, main memory, rotating media, or off-line storage.

The second storage circuit 846 can be a controller of a volatile memory, a nonvolatile memory, an internal memory, an external memory, or a combination thereof. For example, the second storage circuit 846 can be a controller of a nonvolatile storage such as non-volatile random-access memory (NVRAM), Flash memory, disk storage, or a volatile storage such as static random access memory (SRAM).

The second storage interface 848 can receive information from the other functional units/circuits or from external sources or can transmit information to the other functional units/circuits or to external destinations. The external sources and the external destinations refer to sources and destinations external to the second device 106.

The second storage interface 848 can include different implementations depending on which functional units/circuits or external units/circuits are being interfaced with the second storage circuit 846. The second storage interface 848 can be implemented with technologies and techniques similar to the implementation of the second control interface 844.

The second communication circuit 836 can enable external communication to and from the second device 106. For example, the second communication circuit 836 can permit the second device 106 to communicate with the first device 102 over the network 104.

The second communication circuit 836 can also function as a communication hub allowing the second device 106 to function as part of the network 104 and not limited to be an endpoint or terminal unit or circuit to the network 104. The second communication circuit 836 can include active and passive components, such as microelectronics or an antenna, for interaction with the network 104.

The second communication circuit 836 can include a second communication interface 850. The second communication interface 850 can be used for communication between the second communication circuit 836 and other functional units or circuits in the second device 106. The second communication interface 850 can receive information from the other functional units/circuits or can transmit information to the other functional units or circuits.

The second communication interface 850 can include different implementations depending on which functional units or circuits are being interfaced with the second communication circuit 836. The second communication interface 850 can be implemented with technologies and techniques similar to the implementation of the second control interface 844.

The second communication circuit 836 can couple with the network 104 to send information to the first device 102. The first device 102 can receive information in the first communication circuit 816 from the second device transmission 810 of the network 104. The compute system 100 can be executed by the first control circuit 812, the second control circuit 834, or a combination thereof. For illustrative purposes, the second device 106 is shown with the partition containing the second user interface 838, the second storage circuit 846, the second control circuit 834, and the second communication circuit 836, although it is understood that the second device 106 can include a different partition. For example, the second software 842 can be partitioned differently such that some or all of its function can be in the second control circuit 834 and the second communication circuit 836. Also, the second device 106 can include other functional units or circuits not shown in FIG. 8 for clarity.

The functional units or circuits in the first device 102 can work individually and independently of the other functional units or circuits. The first device 102 can work individually and independently from the second device 106 and the network 104.

The functional units or circuits in the second device 106 can work individually and independently of the other functional units or circuits. The second device 106 can work individually and independently from the first device 102 and the network 104.

The functional units or circuits described above can be implemented in hardware. For example, one or more of the functional units or circuits can be implemented using a gate array, an application specific integrated circuit (ASIC), circuitry, a processor, a computer, integrated circuit, integrated circuit cores, a pressure sensor, an inertial sensor, a microelectromechanical system (MEMS), a passive device, a physical non-transitory memory medium containing instructions for performing the software function of the head ailment diagnostic module 115, a portion therein, or a combination thereof.

For illustrative purposes, the compute system 100 is described by operation of the first device 102 and the second device 106. It is understood that the first device 102 and the second device 106 can operate any of the modules and functions of the compute system 100.

Figure 9:
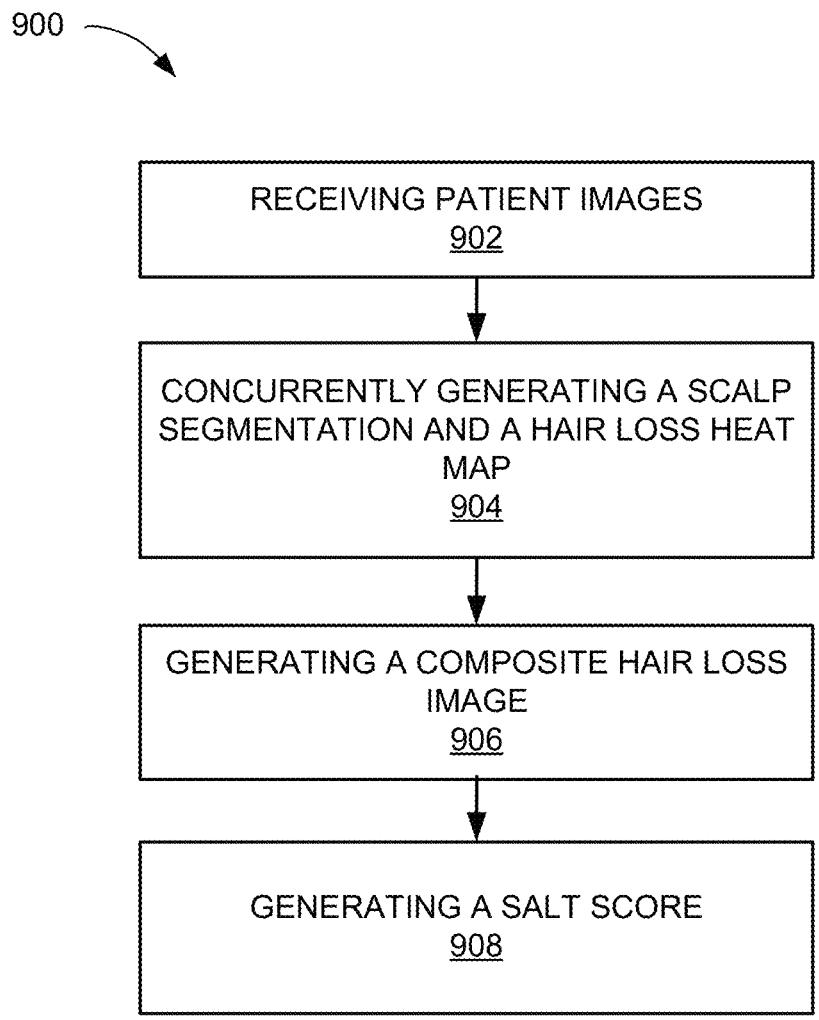
FIG. 9 is a flow chart of a method of operation of a compute system in an embodiment of the present invention.

Referring now to FIG. 9, therein is shown a flow chart of a method 900 of operation of a compute system 100 of FIG. 1 in an embodiment of the present invention. The method 900 includes: receiving patient images by a head ailment artificial intelligence (AI) including a multi-task decoder block in a block 902; concurrently generating a scalp segmentation and a hair loss heat map from the multi-task decoder block of the head ailment AI analyzing the patient images in a block 904; generating a composite hair loss image based on the hair loss heat map and a quadrant computation of the scalp segmentation in a block 906; and generating a SALT score based the hair loss heat map and the composite hair loss image for displaying on a device in a block 908.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of an embodiment of the present invention is that it valuably supports and services the historical trend of reducing costs, simplifying systems, and increasing performance.

These and other valuable aspects of an embodiment of the present invention consequently further the state of the technology to at least the next level.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A method of operation of a compute system comprising:
   receiving patient images by a head ailment artificial intelligence (AI);
   concurrently generating a scalp segmentation and a hair loss heat map by analyzing pixels of the patient images;
   generating a composite hair loss image based on the hair loss heat map and a quadrant computation of the scalp segmentation, wherein the composite hair loss image extends across a border of two or more of a left side image, a right side image, a top image, and a back image; and
   generating a Severity of Alopecia Tool (SALT) score based the hair loss heat map and the composite hair loss image for displaying on a device.

2. The method as claimed in claim 1 wherein receiving the patient image includes receiving the left side image, the right side image, the top image, and the back image.

3. The method as claimed in claim 1 wherein generating the SALT score includes adding a weighted percentage of a scalp area identified by the scalp segmentation.

4. The method as claimed in claim 1 wherein generating the scalp segmentation includes providing a scalp segmentation stream to be processed by analyzing the pixels in the scalp segmentation stream to identify hair loss.

5. The method as claimed in claim 1 wherein generating a hair loss heat map includes providing a heat map stream by processing four of the patient images to generate the percent hair loss of a whole head.

6. The method as claimed in claim 1 further comprising identifying a hair loss factor and scalp area from a pixel group by the head ailment AI already trained.

7. The method as claimed in claim 1 further comprising identifying a hair loss factor to differentiate four levels as normal hair with 0% hair loss, a first stage with 1-33% hair loss, a second stage with 34-66% hair loss, and a final stage with 67-100% hair loss by the head ailment AI already trained.

8. A compute system comprising:
   a control circuit, including a processor, configured to:
   receive patient images by a head ailment artificial intelligence (AI);
   concurrently generate a scalp segmentation and a hair loss heat map by analysis of pixels of the patient images;
   generate a composite hair loss image based on the hair loss heat map and a quadrant computation of the scalp segmentation, wherein the composite hair loss image extends across a border of two or more of a left side image, a right side image, a top image and a back image; and
   generate a Severity of Alopecia Tool (SALT) score based the hair loss heat map and the composite hair loss image for displaying on a device.

9. The system as claimed in claim 8 wherein the control circuit configured to receive the patient image includes the left side image, the right side image, the top image, and the back image received.

10. The system as claimed in claim 8 wherein the control circuit is configured to generate the SALT score includes adding a weighted percentage of a scalp surface identified by the scalp segmentation.

11. The system as claimed in claim 8 wherein the control circuit is configured to generate the scalp segmentation includes a scalp segmentation stream provided to be processed by analyzing the pixels in the scalp segmentation stream to identify hair loss.

12. The system as claimed in claim 8 wherein the control circuit is configured to generate the hair loss heat map includes a heat map stream provided to be processed by processing four of the patient images to generate the percent hair loss of a whole head.

13. The system as claimed in claim 8 wherein the control circuit is further configured to identify a hair loss factor and scalp area from a pixel group by the head ailment AI already trained.

14. The system as claimed in claim 8 wherein the control circuit is further configured to identify a hair loss factor to differentiate four levels as normal hair with 0% hair loss, a first stage with 1-33% hair loss, a second stage with 34-66% hair loss, and a final stage with 67-100% hair loss by the head ailment AI already trained.

15. A non-transitory computer readable medium including instructions executable by a control circuit for a compute system performing functions comprising:
   receiving patient images by a head ailment intelligence (AI);
   concurrently generating a scalp segmentation and a hair loss heat map by analyzing pixels of the patient images;
   generating a composite hair loss image based on the hair loss heat map and a quadrant computation of the scalp segmentation, wherein the composite hair loss image extends across a border of two or more of a left side image, a right side image, a top image, and a back image; and
   generating a Severity of Alopecia Tool (SALT) score based the hair loss heat map and the composite hair loss image for displaying on a device.

16. The non-transitory computer readable medium as claimed in claim 15 wherein receiving the patient image includes receiving the left side image, the right side image, the top image, and the back image.

17. The non-transitory computer readable medium as claimed in claim 15 wherein generating the SALT score includes adding a weighted percentage of a scalp surface identified by the scalp segmentation.

18. The non-transitory computer readable medium as claimed in claim 15 wherein generating the scalp segmentation includes providing a scalp segmentation stream to be processed by analyzing the pixels in the scalp segmentation stream to identify hair loss.

19. The non-transitory computer readable medium as claimed in claim 15 further comprising identifying a hair loss factor and scalp area from a pixel group by the head ailment AI already trained.

20. The non-transitory computer readable medium as claimed in claim 15 further comprising identifying a hair loss factor to differentiate four levels as normal hair with 0% hair loss, a first stage with 1-33% hair loss, a second stage with 34-66% hair loss, and a final stage with 67-100% hair loss by the head ailment AI already trained.

* * * * *